United States Patent
Noon (10) Patent No.: US 12,042,193 B2
(45) Date of Patent: Jul. 23, 2024

(54) STERNAL PLATE WITH RAPID RE-ENTRY

(71) Applicant: DePuy Synthes Products, Inc., Raynham, MA (US)

(72) Inventor: John Noon, Swarthmore, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 17/826,869

(22) Filed: May 27, 2022

(65) Prior Publication Data

US 2022/0378485 A1 Dec. 1, 2022

Related U.S. Application Data

(60) Provisional application No. 63/193,783, filed on May 27, 2021.

(51) Int. Cl.
*A61B 17/80* (2006.01)
*A61B 17/88* (2006.01)
*A61B 17/56* (2006.01)

(52) U.S. Cl.
CPC .......... *A61B 17/8076* (2013.01); *A61B 17/88* (2013.01); *A61B 2017/564* (2013.01)

(58) Field of Classification Search
CPC ... A61B 17/56; A61B 2017/564; A61B 17/80; A61B 17/8028; A61B 17/8076; A61B 17/88
See application file for complete search history.

(56) References Cited

U.S. PATENT DOCUMENTS

| | | | |
|---|---|---|---|
| 6,217,580 B1 * | 4/2001 | Levin | A61B 17/8076 324/532 |
| 7,635,365 B2 * | 12/2009 | Ellis | A61B 17/8076 606/71 |
| 7,803,176 B2 * | 9/2010 | Teague | A61B 17/8076 600/218 |
| 7,871,411 B2 * | 1/2011 | Grevious | A61B 17/8061 606/258 |
| 8,272,613 B2 | 9/2012 | Golle et al. | |
| 8,297,581 B2 | 10/2012 | Golle et al. | |

(Continued)

FOREIGN PATENT DOCUMENTS

DE 102013214937 A1 2/2015

*Primary Examiner* — Larry E Waggle, Jr.
(74) *Attorney, Agent, or Firm* — Kramer & Amado, P.C.

(57) ABSTRACT

A medical fixation system for bone repair including: a first orthopedic plate attached one bone via an inferior surface and a superior surface having a first plurality of sternal plate engagement members; a second orthopedic plate attached to one bone via an inferior surface and a superior surface having a second plurality of sternal plate engagement members; and a third orthopedic plate that bridges the first and second orthopedic plates with a superior surface and an inferior surface having a plurality of bridging plate engagement members; wherein the plurality of bridging plate engagement members is complimentary and opposite to the first and second pluralities of sternal plate engagement members, such that upon contact between the plurality of bridging plate engagement members and the first and second pluralities of sternal plate engagement members, a secure coupling is formed between the first and second orthopedic plates and the third orthopedic plate.

23 Claims, 8 Drawing Sheets

(56) References Cited

U.S. PATENT DOCUMENTS

| | | |
|---|---|---|
| 8,316,516 B2 | 11/2012 | Hoehe et al. |
| 8,898,867 B2 | 12/2014 | Braun et al. |
| 10,022,169 B2 * | 7/2018 | Waizenegger ..... A61B 17/8076 |
| 10,543,027 B2 * | 1/2020 | Frank ................. A61B 17/8076 |
| 2010/0145386 A1 * | 6/2010 | Greenhalgh ....... A61B 17/8863 |
| | | 606/279 |

* cited by examiner

FIG. 7

STERNAL PLATE WITH RAPID RE-ENTRY

CROSS-REFERENCE TO RELATED APPLICATIONS

This application claims benefit to U.S. Provisional Patent Application No. 63/193,783 filed on May 27, 2021, the contents of which are hereby incorporated by reference for all purposes as if fully set forth herein.

TECHNICAL FIELD

Various exemplary embodiments relate generally to surgical reconstruction systems or devices, and more particularly, to devices for reapproximating a patient's sternum subsequent to a sternotomy while allowing rapid and efficient uncoupling of the devices and reopening of the sternal cavity.

BACKGROUND

Many surgical procedures require two or more parts of a sternum to be reapproximated, or fixed together, such as sternal reconstruction or repair of sternal trauma. In addition, various types of surgical procedures are currently performed to investigate, diagnose, and treat diseases involving tissues or organs located in a patient's thoracic cavity, such as the heart and lungs. These procedures typically require a partial or median sternotomy to gain access to the patient's thoracic cavity. A partial or median sternotomy is a procedure by which a saw or other appropriate cutting instrument is used to make a midline, longitudinal incision along a portion or the entire axial length of the patient's sternum, allowing two opposing sternal halves to be separated laterally. A large opening into the thoracic cavity is thus created, through which a surgeon may directly visualize and operate upon the heart and other thoracic organs, vessels, or tissues. Following the surgical procedure within the thoracic cavity, the two severed sternal halves must be reapproximated and compressed, while rigidly maintaining the sternal halves in their reapproximated position relative to each other so that the sternal halves are prevented from moving with respect to each other to promote bone fusion in the weeks following the surgical procedure.

During normal anatomical function, for instance during respiration, body movement, and carrying of objects, forces can be generated that act on the sternum. One conventional system sternal fixation assembly includes stainless steel wires that are placed either parasternally (around the sternum) or transsternally (through the sternum bone) using a cutting needle that is attached to the wire, and subsequently twisted to tighten the wire against the sternum. However, the twisting generates tensile forces onto the wires that tend to weaken the wire, which can result in breakage both during the closure or post-operatively. Furthermore, this type of system relies on the experience of the surgeon when tightening the wires. If the wires are not tightened enough, the sternal compression can be compromised. If the wires are tightened too much, the wire can cut into or through the sternum and/or can break.

Several other techniques of sternal fixation have been developed for reapproximating the sternal halves. One technique uses plates that are located on both sternal halves across the sternotomy and are fixed thereto by means of screws through the bone on either side of the sternotomy. In some examples, the head of the bone screw is locked to the plate (e.g., by threaded engagement between the screw head and the bone plate) and in other plates the head of the screw is free to angulate with respect to the plate, such that the screw may be placed in the bone at a surgeon-selected angle. In yet other examples, the screw head may cooperate with the bone plate to provide compression or distraction of the fragments (i.e., to push the bone fragments towards or away from one another).

Such surgical procedures, especially the case of open heart surgery, can result in patients that are unstable and may require immediate access to the heart postoperatively for emergency reasons. Most of the prior art sternal reapproximation systems do not provide the ability to remove the implants quickly to allow surgical reaccess to the thoracic cavity, and can be a vital contributor to the survival of the patient.

It is desirable to provide an improved clinical solution for sternal closure that provides robust fixation while allowing efficient and effective reopening of the sternal cavity and reapproximation of the sternal closure implant system.

SUMMARY

Accordingly, it would be beneficial to provide a sternal reapproximation plating system that allows secure and efficient sternal reapproximation as well as the ability to quickly provide surgical reaccess to the thoracic cavity without the need to unscrew and remove the surgical hardware.

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a medical fixation system for bone repair including: a first orthopedic plate configured to attach to at least one bone, the first orthopedic plate having an inferior surface configured to contact bone and a superior surface that includes a first plurality of sternal plate engagement members; a second orthopedic plate configured to attach to at least one bone, the second orthopedic plate having an inferior surface configured to contact bone and a superior surface that includes a second plurality of sternal plate engagement members; and a third orthopedic plate configured to bridge the first and second orthopedic plates, the third orthopedic plate having a superior surface and an inferior surface, at least the inferior surface having a plurality of bridging plate engagement members; wherein the plurality of bridging plate engagement members is complimentary and opposite to the first and second pluralities of sternal plate engagement members, such that upon contact between the plurality of bridging plate engagement members and the first and second pluralities of sternal plate engagement members, a secure coupling is formed between the first and second orthopedic plates and the third orthopedic plate.

Various embodiments are described, wherein the first and second pluralities of sternal plate engagement members of the first and second orthopedic plates are formed integrally thereto.

Various embodiments are described, wherein the first and second pluralities of sternal plate engagement members of the first and second plates are coupled thereto.

Various embodiments are described, wherein the first and second pluralities of sternal plate engagement members of the first and second plates are coupled thereto using screws.

Various embodiments are described, wherein the first and second pluralities of sternal plate engagement members of the first and second plates are coupled thereto using adhesive.

Various embodiments are described, wherein the first and second orthopedic plates have a longitudinal axis extending from a lateral end to a medial end, the lateral end configured to be coupled to a patient's ribs and the medial end configured to be coupled to or adjacent to a patient's sternum.

Various embodiments are described, wherein the first and second orthopedic plates includes a first screw hole configured to couple the first and second orthopedic plates to the patients ribs.

Various embodiments are described, wherein the first and second orthopedic plates includes a second screw hole configured to couple the first and second orthopedic plates to the patients sternum.

Various embodiments are described, wherein the first and second pluralities of sternal plate engagement members include two different orientations.

Various embodiments are described, wherein the plurality of bridging plate engagement members include two different orientations complementary to the two different orientation of the first and second pluralities of sternal plate engagement members.

Various embodiments are described, wherein the plurality of bridging plate engagement members and the first and second pluralities of sternal plate engagement members are a metal VELCRO® system.

Various embodiments are described, wherein the plurality of bridging plate engagement members and the first and second pluralities of sternal plate engagement members are a hook and loop system.

Further various embodiments relate to a surgical method using a medical fixation system for bone repair including: a first orthopedic plate configured to attach to at least one bone, the first orthopedic plate having an inferior surface configured to contact bone and a superior surface that includes a first plurality of sternal plate engagement members; a second orthopedic plate configured to attach to at least one bone, the second orthopedic plate having an inferior surface configured to contact bone and a superior surface that includes a second plurality of sternal plate engagement members; and a third orthopedic plate configured to bridge the first and second orthopedic plates, the third orthopedic plate having a superior surface and an inferior surface, at least the inferior surface having a plurality of bridging plate engagement members; wherein the plurality of bridging plate engagement members is complimentary and opposite to the first and second pluralities of sternal plate engagement members, such that upon contact between the plurality of bridging plate engagement members and the first and second pluralities of sternal plate engagement members, a secure coupling is formed between the first and second orthopedic plates and the third orthopedic plate; the method including: performing a sternotomy on a patient resulting in first sternum portion and a second sternum portion; performing a thoracic surgical procedure; closing a ribcage of the patient by placing first sternum portion and second sternum portion in proximity to their presurgical position; attaching the first orthopedic plate to a first rib of the patient; attaching the second orthopedic plate to a second rib of the patient; and fixing the third orthopedic plate to the first and second orthopedic plates.

Various embodiments are described, wherein attaching the first orthopedic plate to the first rib of the patient includes placing a screw in the first rib through a screw hole in the first orthopedic plate.

Various embodiments are described, further including attaching the first orthopedic plate to the first sternum portion.

Various embodiments are described, wherein attaching the first orthopedic plate to the first sternum portion includes placing a screw in the first sternum portion through a screw hole in the first orthopedic plate.

Various embodiments are described, wherein the plurality of bridging plate engagement members and the first and second pluralities of sternal plate engagement members are a metal VELCRO® system.

Various embodiments are described, wherein the plurality of bridging plate engagement members and the first and second pluralities of sternal plate engagement members are a hook and loop system.

Further various embodiments relate to a surgical method using a medical fixation system for bone repair implanted in a patient, wherein the medical fixation system includes: a first orthopedic plate configured to attach to at least one bone, the first orthopedic plate having an inferior surface configured to contact bone and a superior surface that includes a first plurality of sternal plate engagement members; a second orthopedic plate configured to attach to at least one bone, the second orthopedic plate having an inferior surface configured to contact bone and a superior surface that includes a second plurality of sternal plate engagement members; and a third orthopedic plate configured to bridge the first and second orthopedic plates, the third orthopedic plate having a superior surface and an inferior surface, at least the inferior surface having a plurality of bridging plate engagement members; wherein the plurality of bridging plate engagement members is complimentary and opposite to the first and second pluralities of sternal plate engagement members, such that upon contact between the plurality of bridging plate engagement members and the first and second pluralities of sternal plate engagement members, a secure coupling is formed between the first and second orthopedic plates and the third orthopedic plate; the method including: exposing the implanted medical fixation system; removing the third orthopedic plate from the first and second orthopedic plates; opening a ribcage of the patient; performing a thoracic surgical procedure; closing a ribcage of the patient by placing first sternum portion and second sternum portion in proximity to their presurgical position; and fixing the third orthopedic plate to the first and second orthopedic plates.

Various embodiments are described, wherein removing the third orthopedic plate from the first and second orthopedic plates includes removing the third orthopedic plate by hand.

Various embodiments are described, wherein removing the third orthopedic plate from the first and second orthopedic plates includes removing the third orthopedic plate using a tool.

Various embodiments are described, wherein the plurality of bridging plate engagement members and the first and second pluralities of sternal plate engagement members are a metal VELCRO® system.

Various embodiments are described, wherein the plurality of bridging plate engagement members and the first and second pluralities of sternal plate engagement members are a hook and loop system.

The disclosure is directed to a sternum fixation device for securing parts of a sternum. The sternum fixation system includes a first plate, a second plate, and a third bridging plate. The first orthopedic plate has an upper surface and a bone-contacting surface, a lateral end and a medial end, at least one hole passing through the upper and bone-contacting surfaces for receiving a fastener head of a bone fastener, and a metal VELCRO® segment disposed atop or coupled to the superior surface and adjacent the medial end. The at least one hole may be threaded to receive a threaded fastener head. The second orthopedic plate has an upper surface and a bone-contacting surface, a lateral end and a medial end, at least one hole passing through the upper and bone-contacting surfaces for receiving a fastener head of a bone fastener, and a metal VELCRO® segment disposed atop or coupled to the superior surface and adjacent the medial end. The at least one hole may be threaded to receive a threaded fastener head. The third bridging plate has an upper surface and an under surface configured to contact the upper surfaces of the first and second plates. At least the under surface includes a metal VELCRO® segment. The metal VELCRO® segment of the first and second plate is chosen from one of a plurality of hook-like and catch-like or loop-like forms, while the metal VELCRO® portion of the third bridging plate is chosen to be the complimentary to and opposite that chosen for the first and second plates, such that the hook-like and catch-like or loop-like forms securely couple the first orthopedic plate to the second orthopedic plate via the third bridging plate and securely reapproximate the sternum.

Metaklett (from German Metall, "metal" and Klettband, "VELCRO® ribbon"), or hereafter metallic VELCRO®, is a fastening material made of steel that acts on a similar principle to conventional hook and loop fasteners. It was developed by Reinz-Dichtungs-GmbH, Technische Universität München, Hölzel Stanz-und Feinwerktechnik GmbH & Co. KG and Koenig Verbindungstechnik GmbH. Metaklett and, depending on its designed configuration, can support shear strengths up to 35 tons per square meter. It includes two complementary strips of perforated steel with catches and holes. A second known variant includes two strips with protruding brushes and hooks.

The orthopedic plates of the medical implants disclosed herein may be made of biocompatible metals, biocompatible resorbable and/or non-resorbable polymers, or a combination thereof. Suitable materials include but are not limited to polyetheretherketone (PEEK), polyetherketoneketone (PEKK), titanium, or stainless steel. The orthopedic plates described herein can be configured to attach to at least one bone and may include at least one threaded opening that extends through the orthopedic plates.

BRIEF DESCRIPTION OF THE DRAWINGS

The drawings illustrate generally, by way of example, but not by way of limitation, various embodiments discussed in the present disclosure. The foregoing summary, as well as the following detailed description of preferred embodiments of the application, will be better understood when read in conjunction with the appended drawings.

To facilitate understanding, identical reference numerals have been used to designate elements having substantially the same or similar structure and/or substantially the same or similar function.

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

The present disclosure describes medical implants that may be used to close and secure a sternotomy subsequent to thoracic surgery and further allow subsequent rapid reopening and reapproximation of the sternum.

Figure 1:
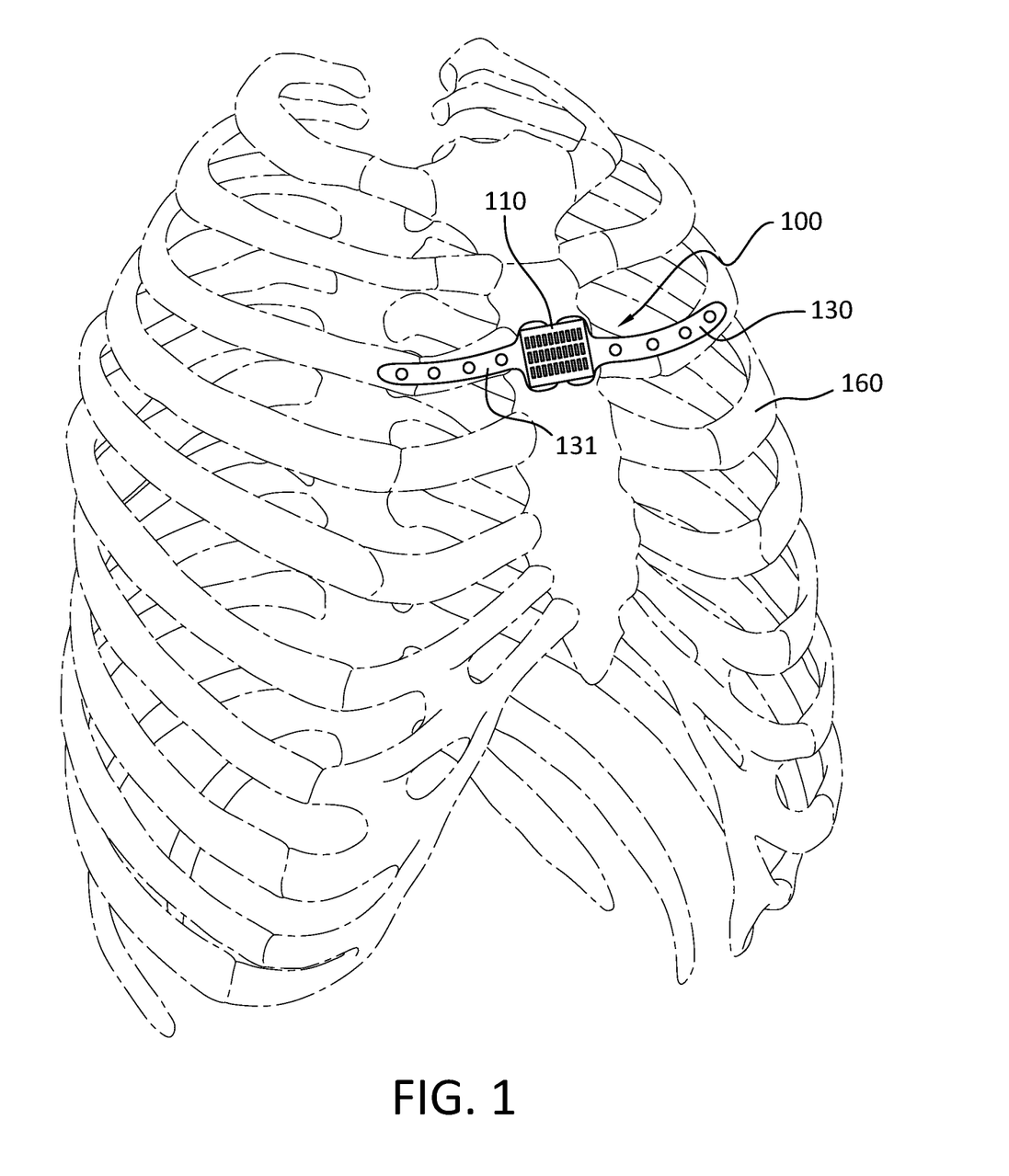
FIG. 1 illustrates the application of a bone fixation system.
Figure 2A:
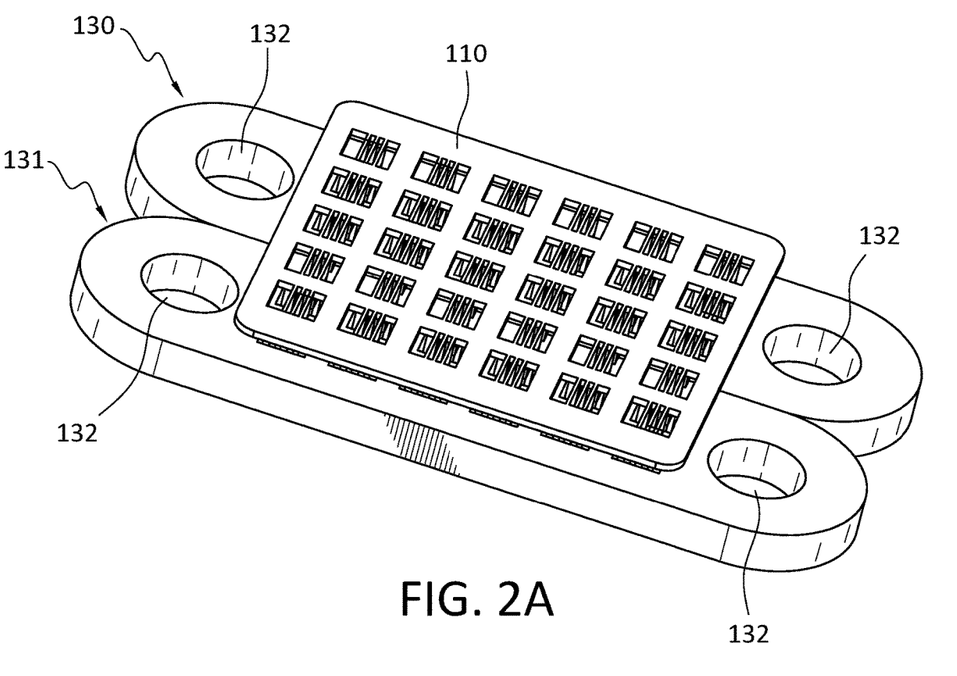
FIGS. 2A-2C illustrate top, bottom, and side perspective views of the combination of the bridging plate and the sternum plate (see FIG. 5).
Figure 2B:
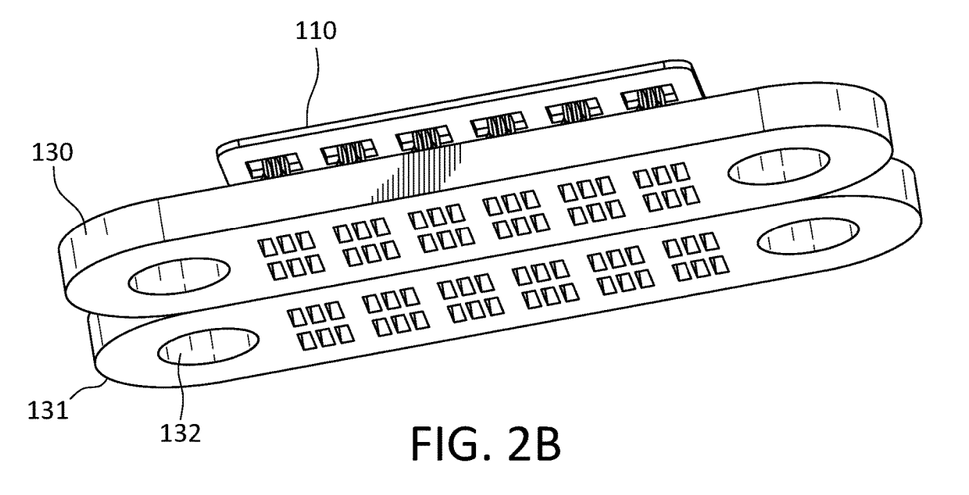
Figure 2C:
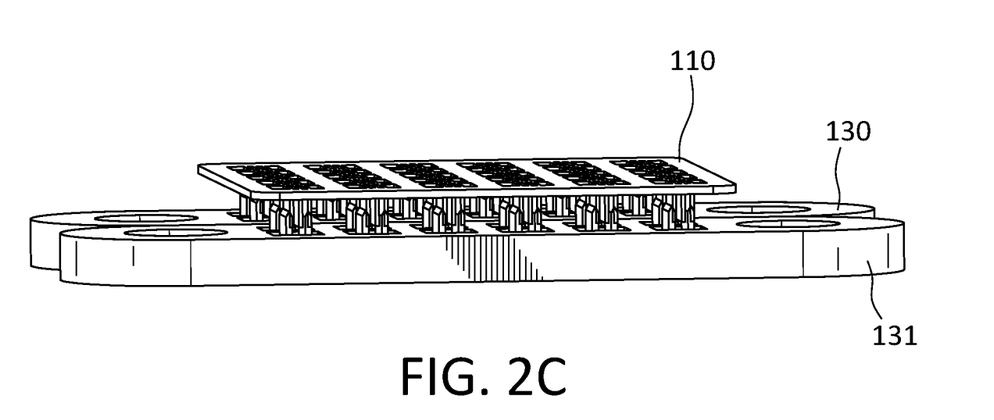
Figure 2D:
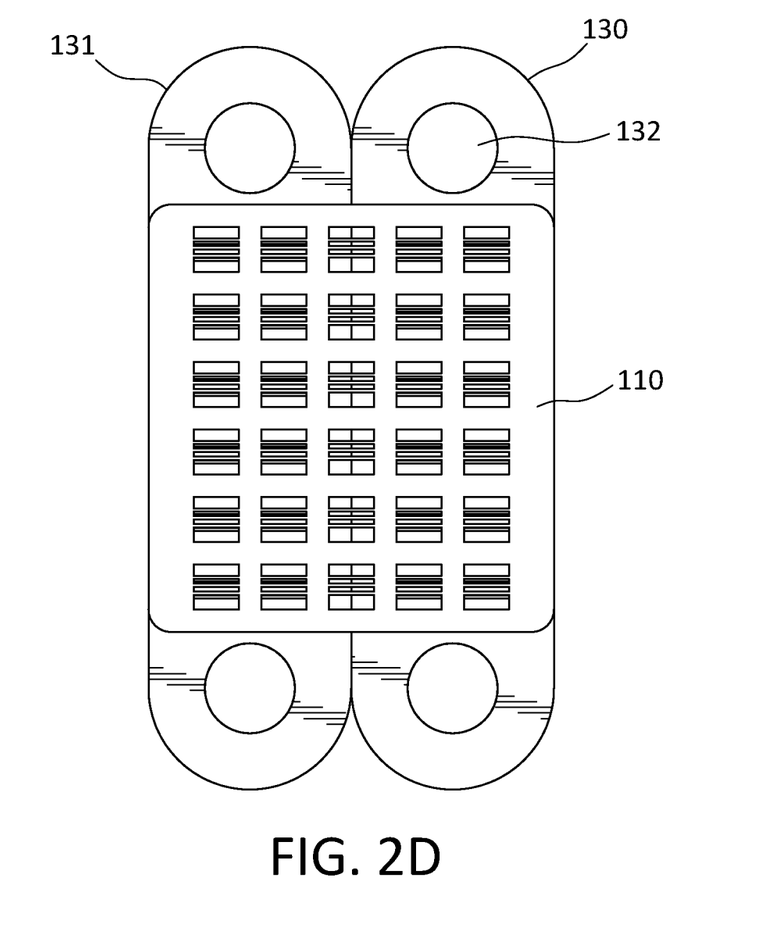
FIG. 2D illustrates a top view of the combination of the bridging plate and the sternum plate.

FIG. 1 illustrates the application of a bone fixation system 100. The bone fixation system 100 includes a first sternal plate 131, a second sternal plate 130, and a bridging plate 110. FIGS. 2A-2C illustrate top, bottom, and side perspective views of the combination of the bridging plate 110 and the sternum plate 138 (see FIG. 5). In one preferred embodiment, the first and second sternal plates 131 and 130 are identical or mirror-symmetrical, such as may be desirable when a vertical sternotomy is performed. The first and second sternal plates 131 and 130 include a long axis extending from a lateral end to a medial end and include an inferior bone-facing surface and an opposite, superior surface. The first and second sternal plates 131 and 130 are configured to be disposed on opposite sides of the sternotomy cut and, in one embodiment, are configured to extend laterally along one or more of the patient's ribs and medially toward the center of the patient's sternum. The plates 131 and 130 include a plurality of rib screw holes 142 along at least a portion of their length configured to accommodate bone anchors into the bone of the patient's rib(s), and in some embodiments, there are also sternum screw holes 132 at or adjacent to the medial ends of the first and second sternal plates 131 and 130 configured to accommodate bone anchors into the bone of the patient's sternum. At least a portion of the superior surface of first and second sternal plating segments 131 and 130 includes a metallic VELCRO® segment coupled adjacent to or formed integral to and monolithically with the medial ends thereof.

Figure 3A:
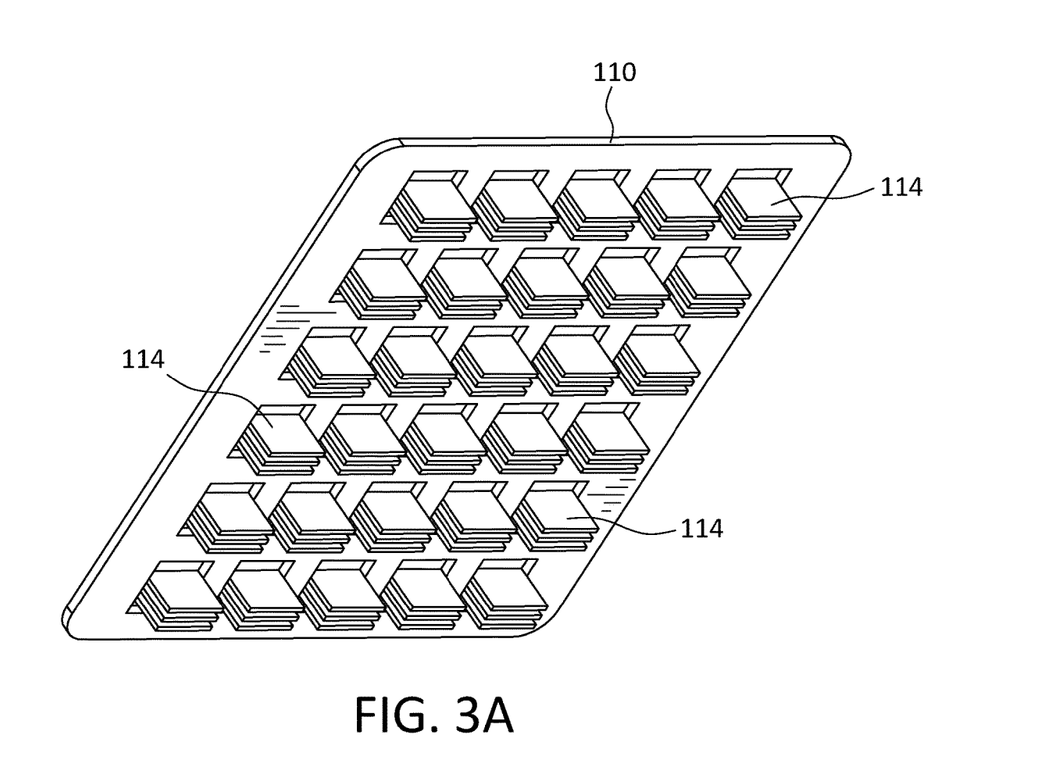
FIGS. 3A and 3B illustrate perspective views of the inferior surface and superior surface of the bridging plate respectively.
Figure 3B:
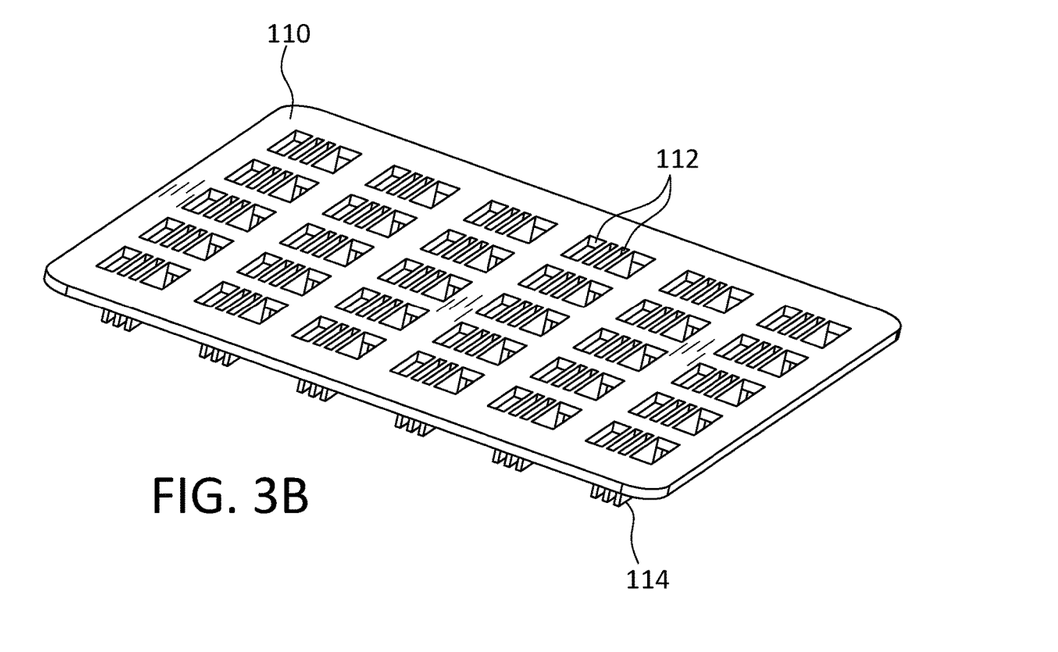

FIGS. 3A and 3B illustrate perspective views of the inferior surface and superior surface of the bridging plate 110 respectively. The bridging plate 110 includes a superior surface and an opposite, inferior surface. At least the inferior surface of the bridging plate 110 includes a metallic VELCRO® portion that is configured to mate with the complimentary metallic VELCRO® coupled to or integral to the first and second sternal plates 131 and 130. The bridging plate 110 includes plate engagement members 114 extending from the interior surface that act as a portion of the metallic VELCRO®. The bridging plate 110 also includes bridging plate openings 112 that surround the bridging plate engagement members 114 and that facilitate interaction with the metallic VELCRO® elements on the first sternal plate 130.

Figure 4A:
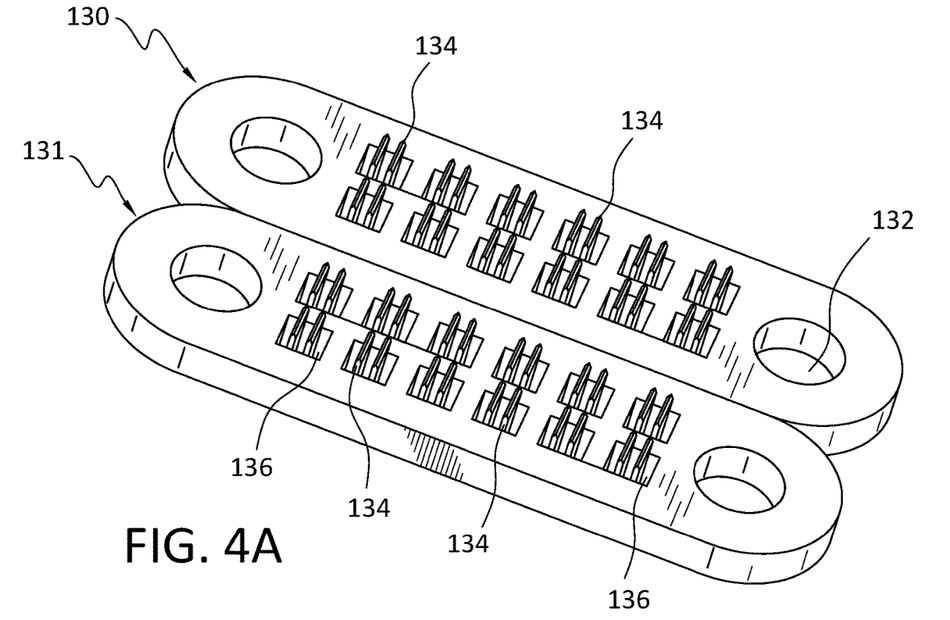
FIGS. 4A-C illustrate top, bottom, and side perspective views of the sternum plates of the first sternal plate and sternum screw hole adjacent to one another.
Figure 4B:
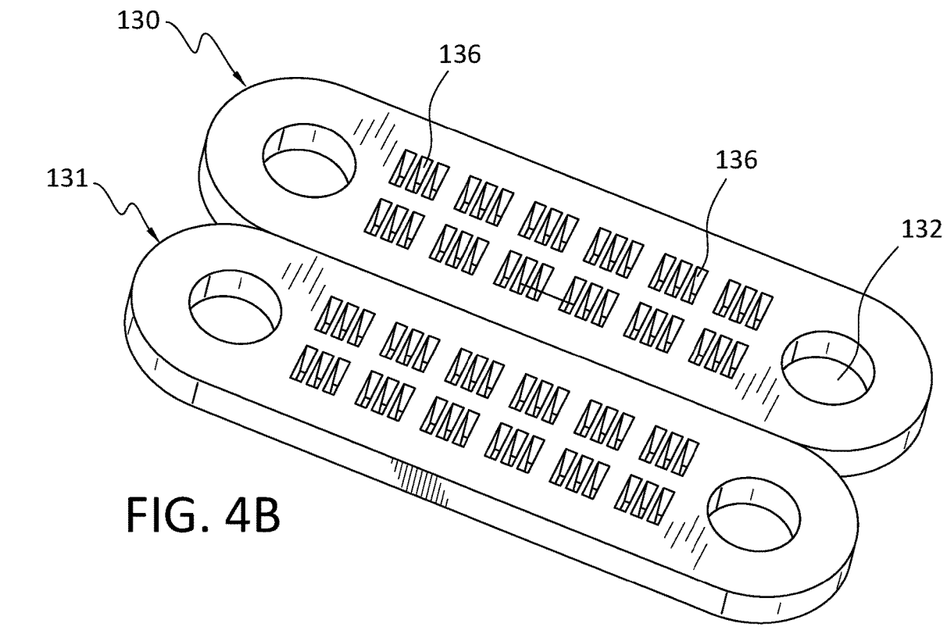
Figure 4C:
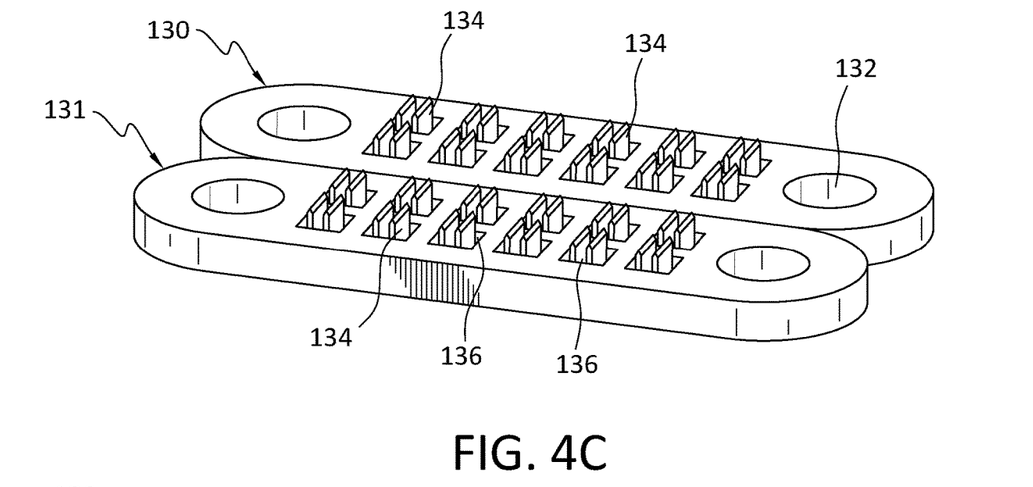
Figure 5:
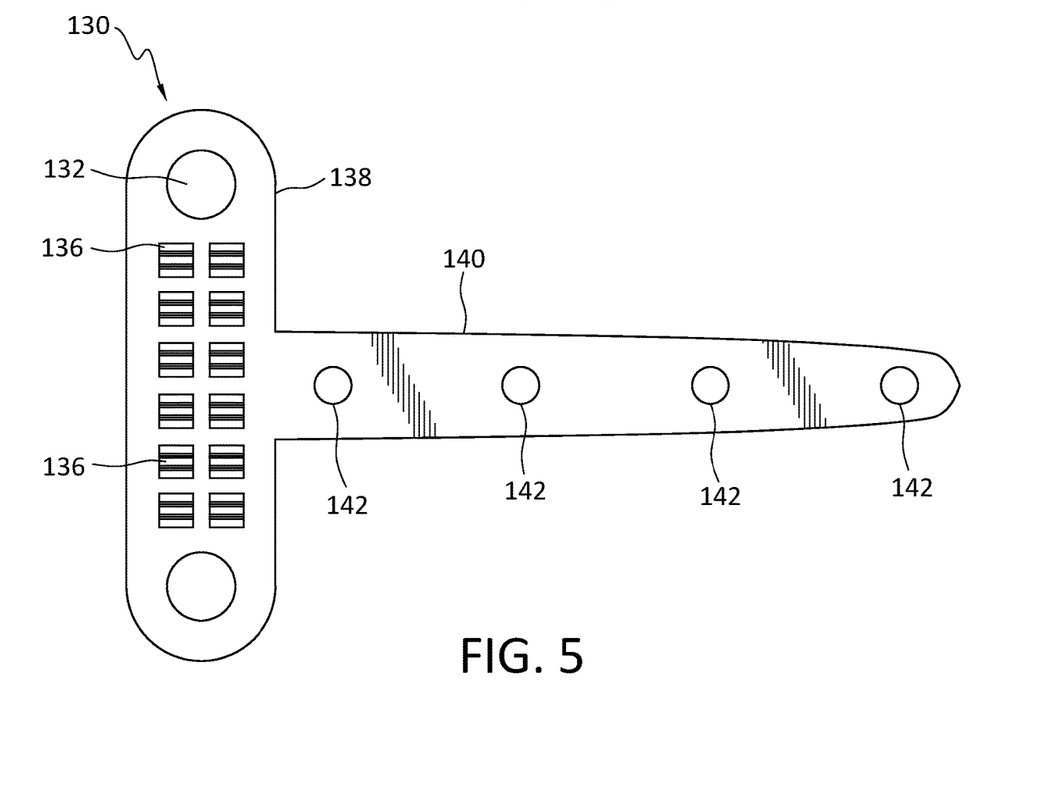
FIG. 5 illustrates a top view of the first sternal plate.

FIG. 4 illustrates a top view of the first sternal plate 130. The first sternal plate 130 includes sternum hole 132, sternal plate engagement members 134, sternal plate opening 136, sternum plate 138, rib plate 140, and rib screw hole 142. FIGS. 5A-C illustrate top, bottom, and side perspective views of the sternum plates 138 of the first sternal plate 130 and second sternal plate 131 adjacent to one another. The first sternal plate 130 includes the rib plate 140 connected to the sternum plate 138. The rib plate 140 is configured to extend along a patient rib in the patient rib cage 160. The rib plate 140 may be curved to generally match the curve of a typical rib. Further, the rib plate 140 may be bent to better match a specific patient's rib.

The sternum plate 138 is configured to attach to a patient's sternum. The sternum plate 138 may include sternum screw hole(s) 132 to facilitate a connection to the patient's sternum. In some embodiments, the sternum screw hole(s) 132 may not be present and the rib screw holes 142 fix the first sternal plate 130 to the patient. The sternum plate 138 also includes sternal plate engagement members 134 that act as a portion of the metallic VELCRO® configured to engage bridging plate engagement members 114 on the bridging plate 110. The first sternal plate 130 includes sternal plate opening 136 that facilitate the engagement with bridging plate engagement members 114. FIG. 2C illustrates the interaction and engagement between bridging plate engagement members 114 and sternal plate engagement members 134. Specifically, the bridging plate engagement members 114 may be spaced apart from one another so as to capture the sternal plate engagement members 134. Likewise, the sternal plate engagement members 134 may be spaced apart from one another so as to capture the bridging plate engagement members 114. This arrangement may provide sufficient lateral force to keep first sternal plate 130 and second sternal plate 131 together adjacent to one another and hence to keep the two parts of the cut sternum together. Further, while bridging plate engagement members 114 and sternal plate engagement members 134 are show as all being oriented in the same first direction, a portion may be oriented in another direction such as substantially perpendicular to the first direction. This mixture of orientations will provide resistance to lateral shear forces in all directions. Further, the sternal plate engagement members 134 are shown in groups of two, and the bridging plate engagement members 114 are shown in groups of three. These groups may be other sizes as well in order to facilitate the engagement of the bridging plate 110 to the first sternal plate 130 and second sternal plate 131.

The sternum screw holes 132 and rib screw holes 142 may be threaded or unthreaded to accommodate a variety of different types of screws including those with threaded heads. Further, the sternum screw holes 132 and rib screw holes 142 may be configured to accommodate the insertion of screws at various angles to provide the surgeon with increased flexibility in screw placement including holes that may urge the bones together or apart as the screws are tightened.

In one embodiment, the medial end including the sternum plate 138 is characterized by a width that is larger than that which characterizes the lateral end including the rib plate 140. In an alternate embodiment, the width of the sternum plate 138 and the rib plate 140 are essentially consistent the entire length of the first sternal plate 130 from its lateral to medial end.

Figure 6A:
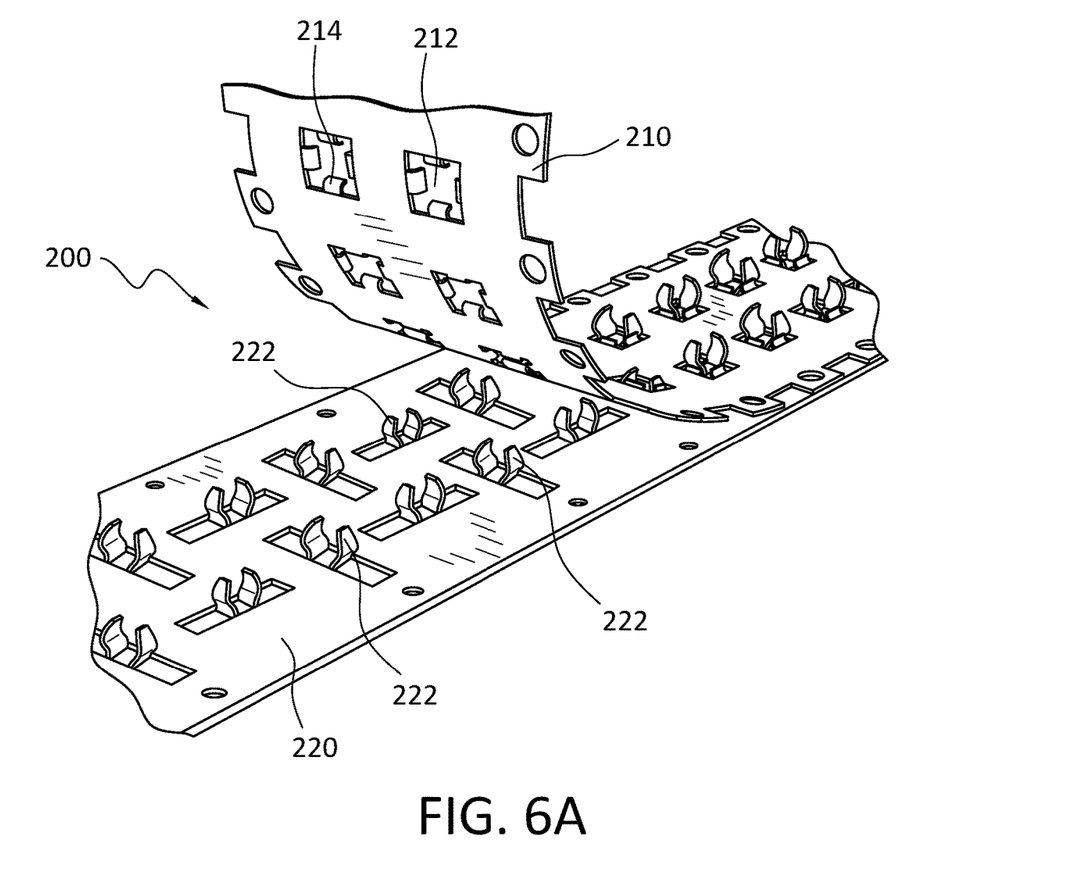
FIGS. 6A-6C illustrate a second metallic VELCRO® implementation.
Figure 6B:
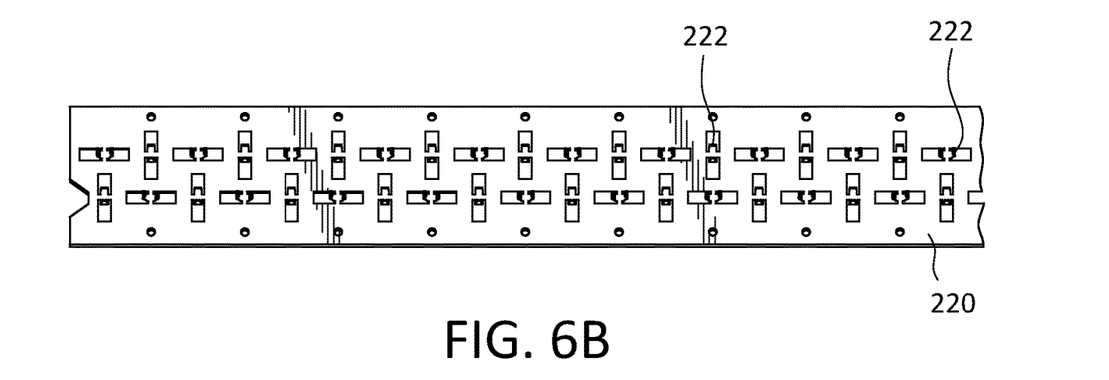
Figure 6C:
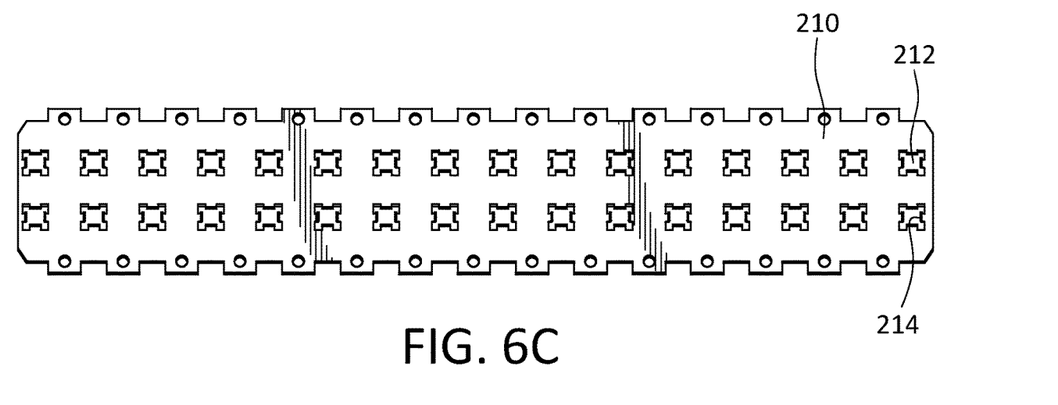

The bone fixation system 100 described in FIGS. 1-5 include one specific implementation of metallic VELCRO®. Other implementations of metallic VELCRO® may be used as well. FIGS. 6A-6C illustrate a second metallic VELCRO® implementation. In the second implementation, the bridging plate 110 is provided in the form of a first VELCRO® portion 210 that is a thin metallic strip that includes a plurality of VELCRO® openings 212 in the form of through-holes or blind-holes disposed therethrough. The edges of the VELCRO® openings 212 may include VELCRO® opening tabs 214 that serve as catches to the VELCRO® engagement members 222 which may be hook-like forms extending from second VELCRO® portion 220. The VELCRO® engagement members 222 may be configured in pairs where a pair of VELCRO® engagement members 222 engage one VELCRO® opening 212. The VELCRO® engagement members 222 may have a bent or hook-like shape so that their ends bend towards one another to facilitate insertion into VELCRO® opening 212. As the ends of VELCRO® engagement members 222 enter the VELCRO® opening 212, the VELCRO® engagement members 222 flex towards one another, and then return to their previous position when a bent portion of the VELCRO® engagement members 222 passes the VELCRO® opening tabs 214. This bent portion of the VELCRO® engagement members 222 engages the VELCRO® opening tab 214 to secure the first VELCRO® portion 210 to the second VELCRO® portion 220. The second VELCRO® portion 220 may be coupled to or integral to the first and second sternal plates 131 and 130. In an alternate embodiment, the first and second sternal plates 131 and 130 include a plurality of openings in the form of through-holes or blind-holes disposed therethrough, the openings serving as catches to hook-like forms extending from the inferior surface of the bridging plate 110.

In yet another embodiment, the inferior surface of the bridging plate 110 includes at least a portion upon which is disposed or coupled one of a plurality of hooks or loops extending inferiorly therefrom, configured to mate with a complimentary plurality of hooks or loop extending superiorly from the superior surface of the first and second sternal plates 131 and 130. In such an embodiment, the more conventional VELCRO® configuration of hooks and loops may be formed of metal or may be formed of a biocompatible polymers or other, biocompatible non-metallic materials.

Figure 7:
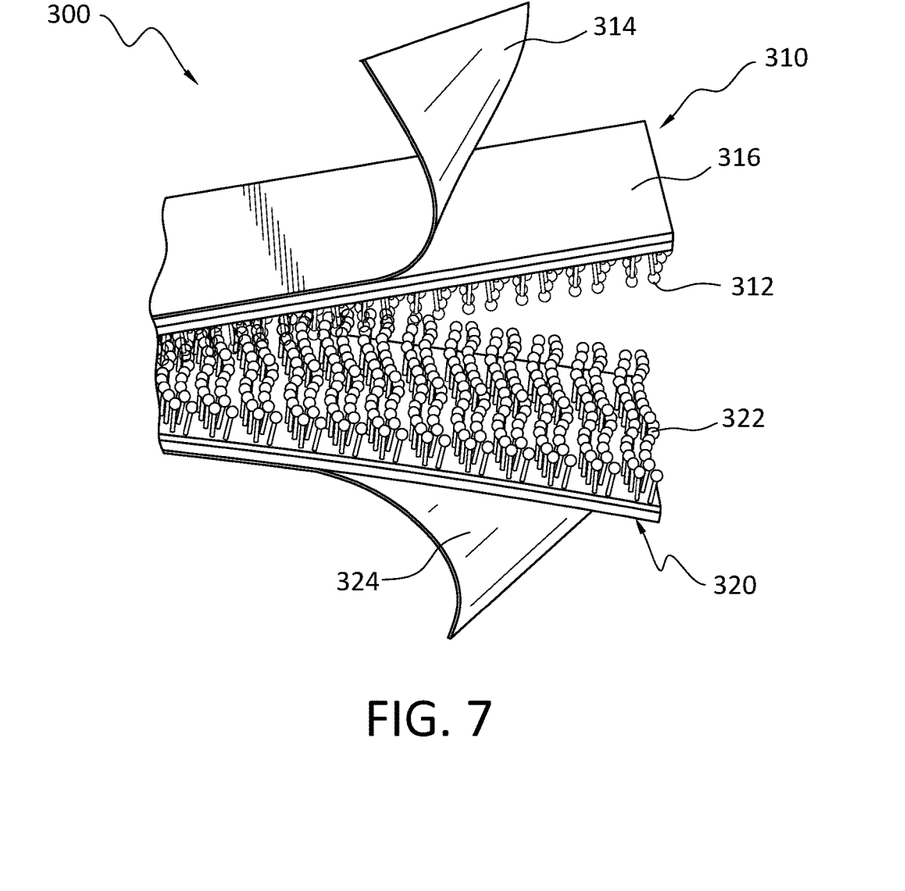
FIG. 7 illustrates a second metal VELCRO® implementation.

FIG. 7 illustrates a second metal VELCRO® implementation. This implementation my include first VELCRO® portion 310 and second VELCRO® portion 320. The first VELCRO® portion 310 may include first VELCRO® engagement members 312, first VELCRO® adhesive layer 316, and first VELCRO® backing 314. Likewise, second VELCRO® portion 320 may include second VELCRO® engagement members 322, second VELCRO® adhesive layer (not shown), and second VELCRO® backing 324. The first VELCRO® engagement members 312 and second VELCRO® engagement members 322 are configured to have a shaft with a head at the end that has a diameter larger than the diameter of the shaft. Further, first VELCRO® engagement members 312 and second VELCRO® engagement members 322 are arranged in complementary rows that allow the opposing members to engage and capture one another. The first VELCRO® portion 310 and second VELCRO® portion 320 may include an adhesive layer (e.g., first VELCRO® adhesive layer 316) that allows the first VELCRO® engagement member 312 to be attached to first sternal plate 130 and the second VELCRO® engagement member 322 to be attached to a bridging plate.

Any other type of metallic VELCRO® may also be used instead of the implementations described above. Further, non-metallic VELCRO® or hook and loop implementations may be used in the bone fixation system 100. Any such implementation may be used as long as it is biocompatible and sufficiently able to withstand the forces associated with binding the sternum back together.

The metallic VELCRO® portion disposed on the superior surface of the first and second sternal plates 131 and 130 may be pre-assembled thereto, or secured thereto preoperatively or intra-operatively, via any suitable biocompatible mechanical coupling mechanisms such as screws, staples, rivets, pins, or press-fitting into grooves in the plate. or via a biocompatible adhesive, or laser welded thereto. In one preferred embodiment, metallic VELCRO® segments in the form of thin metallic strips are coupled atop the first and second plate segments via screws into the existing screw holes at or near the medial ends of the first and second sternal plates 131 and 130. Alternately, adhesive-backed tape-like forms of VELCRO®, metallic or polymeric, as shown in FIGS. 6A-6C or FIG. 7, may be applied pre-operatively or intra-operatively atop the medial portions of the first and second sternal plates 131 and 130. Alternately, the metallic VELCRO® segments disposed on the superior surface of the first and second sternal plates 131 and 130 may be inherent and monolithic thereto, and may be formed by 3-D printing or other additive manufacturing process, or may be machined from a blank.

The first and second sternal plating segments have a preferred thickness in a range between 0.5 mm to 4.0 mm, while the bridging plate has a preferred thickness in the range of 0.1 mm to 3.0 mm.

In operation, and in continued reference to FIGS. 1-7, a sternotomy is created to provide access to a patient's thoracic cavity. The sternotomy may be a standard incision through the sternum extending from the superior portion of the sternum vertically down the sternum and xiphoid process. Alternately, the sternal incision(s) may include one or more mini-sternotomies, transverse sternotomies, and J-cut sternotomies, or combinations thereof. The ribcage is then spread open to allow surgical access to the thoracic cavity.

A thoracic surgical procedure is then performed by a surgeon and, upon completion of the procedure, the ribcage is then closed and the split sternal portions are placed in close proximity to their original, presurgical position. The first and second sternal plates 131 and 130 are then secured to the ribs and/or breastbone, e.g., via screw fixation through the sternum screw holes 132 and rib screw holes 142 of the first and second sternal plate 131 and 130 and into the underlying bone of the ribs and, in some embodiments, also the sternum. In an alternate embodiment, the first and second sternal plates 131 and 130 are secured to the ribs and/or sternum of the patient prior to the sternotomy and thoracic intervention. The surgeon then applies compression to either side of the sternotomy cut, in one embodiment by using an instrument to draw the first and second sternal plate segments into proximity with one another, and couples the bridging plate 110 to the medial portions of the first and second sternal plates 131 and 130, securing the complementary bridging plate engagement members 114 and sternal plate engagement members 134 to one another to thereby lock the bone fixation system 100 and reapproximate the severed sternum.

Subsequent to the reapproximation of the severed sternum, the nature of the bridging plate engagement members 114 and sternal plate engagement members 134 (or other VELCRO® or metallic VELCRO®) inherent to the bone fixation system 100 enables rapid and relatively effortless uncoupling of the first and second sternal plates 131 and 130 and the bridging plate 110, and thereby reopening of the severed sternum, to allow surgical reaccess to the thoracic cavity for further surgical intervention or to allow additional reapproximation of the severed sternum. The uncoupling of the bridging plate 110 from the first and second sternal plates 131 and 130 can be accomplished by coupling a forceps-type instrument to the bridging plate 110 and applying a lifting or peeling motion, for example. Alternately, the surgeon may simply peel the bridging plate 110 from the first and second sternal plate segments 131 and 130 using their fingers.

It will be understood by those having ordinary skill in the art that various manufacturing methods may be used to make the medical implants of the invention. The medical implants may be 3D printed via additive manufacturing, subtractive manufacturing, or a combination thereof. In the alternative, the medical implants described herein can be injection molded or stamped and cut from a flat sheet and formed to the anatomical shape either during manufacture or in a clinic on an anatomical model.

It will be understood by those having ordinary skill in the art that the term metallic VELCRO® may encompass a variety of material compositions, including any biocompatible metal, such as titanium, TAN, and stainless steel. Further, it is envisioned in some embodiments that non-metallic VELCRO®-like materials may be substituted without compromising the strength and stability of the bone fixation system 100, and may be formed of biocompatible polymers such as PEEK, PEKK, resorbable polymers, or other biocompatible materials.

The medical implants of this disclosure may be pre-designed such that they are ready to use "off the shelf." Pre-designed implants may be moldable or shaped by the user to fit the patient. In other embodiments, the pre-designed medical implants may be trimmed by the user to the near net shape of the patient.

In yet another embodiment, the medical implants of the disclosure may be designed to be patient specific via 3D printing according to a surgical plan. In this process, a clinician or engineer may use DICOM® (Digital Imaging and Communications in Medicine) data of a patient to create a 3D implant design using digital, semi-automated software. Points could be placed along the surface of a filled defect (or splines that create the desired shape). Orthopedic plates could then be positioned on those points, with the bone facing surface of the plates "normal to" the surface of the bone. The external surfaces of the assembly can be shaped to follow the patient anatomical ribs and/or breastbone.

Further, implementations of the bone fixation system 100 are describe above relative to the sternum. The bone fixation system 100 may also be applied to other bone structures in the body, including for example, the cranium.

While each of the embodiments are described above in terms of their structural arrangements, it should be appreciated that the invention also covers the associated methods of using the embodiments described above.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications and combinations of the various embodiments can be affected while remaining within the spirit and scope of the invention. Accordingly, the foregoing disclosure, description, and figures are for illustrative purposes only and do not in any way limit the invention, which is defined only by the claims.

What is claimed:

1. A medical fixation system for bone repair comprising:
   a first orthopedic plate configured to attach to at least one bone, the first orthopedic plate having an inferior surface configured to contact bone and a superior surface that includes a first plurality of sternal plate engagement members that extend away from the first orthopedic plate and from the inferior surface of the first orthopedic plate;
   a second orthopedic plate configured to attach to at least one bone, the second orthopedic plate having an inferior surface configured to contact bone and a superior surface that includes a second plurality of sternal plate engagement members that extend away from the second orthopedic plate and from the inferior surface of the second orthopedic plate; and
   a third orthopedic plate configured to bridge the first and second orthopedic plates, the third orthopedic plate having a superior surface and an inferior surface, at least the inferior surface having a plurality of bridging plate engagement members that extend away from the third orthopedic plate;
   wherein the plurality of bridging plate engagement members is complimentary and opposite to the first and second pluralities of sternal plate engagement members, such that upon contact between the plurality of bridging plate engagement members and the first and second pluralities of sternal plate engagement members, a secure coupling is formed between the first and second orthopedic plates and the third orthopedic plate.

2. The medical fixation system of claim 1, wherein the first and second pluralities of sternal plate engagement members of the first and second orthopedic plates are formed integrally thereto.

3. The medical fixation system of claim 1, wherein the first and second pluralities of sternal plate engagement members of the first and second plates are coupled thereto.

4. The medical fixation system of claim 3, wherein the first and second pluralities of sternal plate engagement members of the first and second plates are coupled thereto using screws.

5. The medical fixation system of claim 3, wherein the first and second pluralities of sternal plate engagement members of the first and second plates are coupled thereto using adhesive.

6. The medical fixation system of claim 1, wherein the first and second orthopedic plates have a longitudinal axis extending from a lateral end to a medial end, the lateral end configured to be coupled to a patient's ribs and the medial end configured to be coupled to or adjacent to a patient's sternum.

7. The medical fixation system of claim 6, wherein the first and second orthopedic plates include a first screw hole configured to couple the first and second orthopedic plates to the patient's ribs.

8. The medical fixation system of claim 7, wherein the first and second orthopedic plates include a second screw hole configured to couple the first and second orthopedic plates to the patient's sternum.

9. The medical fixation system of claim 1, wherein the first and second pluralities of sternal plate engagement members include two different orientations.

10. The medical fixation system of claim 9, wherein the plurality of bridging plate engagement members include two different orientations complementary to the two different orientations of the first and second pluralities of sternal plate engagement members.

11. The medical fixation system of claim 1, wherein the plurality of bridging plate engagement members and the first and second pluralities of sternal plate engagement members are a metal hook and loop system.

12. The medical fixation system of claim 1, wherein the plurality of bridging plate engagement members and the first and second pluralities of sternal plate engagement members are a hook and loop system.

13. A surgical method using a medical fixation system for bone repair including, wherein the medication fixation system includes:
   a first orthopedic plate configured to attach to at least one bone, the first orthopedic plate having an inferior surface configured to contact bone and a superior surface that includes a first plurality of sternal plate engagement members that extend away from the first orthopedic plate and from the inferior surface of the first orthopedic plate;
   a second orthopedic plate configured to attach to at least one bone, the second orthopedic plate having an inferior surface configured to contact bone and a superior surface that includes a second plurality of sternal plate engagement members that extend away from the second orthopedic plate and from the inferior surface of the second orthopedic plate; and
   a third orthopedic plate configured to bridge the first and second orthopedic plates, the third orthopedic plate having a superior surface and an inferior surface, at least the inferior surface having a plurality of bridging plate engagement members that extend away from the third orthopedic plate;
   wherein the plurality of bridging plate engagement members is complimentary and opposite to the first and second pluralities of sternal plate engagement members, such that upon contact between the plurality of bridging plate engagement members and the first and second pluralities of sternal plate engagement members, a secure coupling is formed between the first and second orthopedic plates and the third orthopedic plate;
   the method comprising:
     performing a sternotomy on a patient resulting in a first sternum portion and a second sternum portion;
     performing a thoracic surgical procedure;
     closing a ribcage of the patient by placing first sternum portion and second sternum portion in proximity to their presurgical position;
     attaching the first orthopedic plate to a first rib of the patient;
     attaching the second orthopedic plate to a second rib of the patient; and fixing the third orthopedic plate to the first and second orthopedic plates.

14. The method of claim 13, wherein attaching the first orthopedic plate to the first rib of the patient includes placing a screw in the first rib through a screw hole in the first orthopedic plate.

15. The method of claim 13, further comprising attaching the first orthopedic plate to the first sternum portion.

16. The method of claim 15, wherein attaching the first orthopedic plate to the first sternum portion includes placing a screw in the first sternum portion through a screw hole in the first orthopedic plate.

17. The method of claim 13, wherein the plurality of bridging plate engagement members and the first and second pluralities of sternal plate engagement members are a metal hook and loop system.

18. The method of claim 13, wherein the plurality of bridging plate engagement members and the first and second pluralities of sternal plate engagement members are a hook and loop system.

19. A surgical method using a medical fixation system for bone repair implanted in a patient, wherein the medical fixation system includes:
   a first orthopedic plate configured to attach to at least one bone, the first orthopedic plate having an inferior surface configured to contact bone and a superior surface that includes a first plurality of sternal plate engagement members that extend away from the first orthopedic plate and from the inferior surface of the first orthopedic plate;
   a second orthopedic plate configured to attach to at least one bone, the second orthopedic plate having an inferior surface configured to contact bone and a superior surface that includes a second plurality of sternal plate engagement members that extend away from the second orthopedic plate and from the inferior surface of the second orthopedic plate; and
   a third orthopedic plate configured to bridge the first and second orthopedic plates, the third orthopedic plate having a superior surface and an inferior surface, at least the inferior surface having a plurality of bridging plate engagement members that extend away from the third orthopedic plate;
   wherein the plurality of bridging plate engagement members is complimentary and opposite to the first and second pluralities of sternal plate engagement members, such that upon contact between the plurality of bridging plate engagement members and the first and second pluralities of sternal plate engagement members, a secure coupling is formed between the first and second orthopedic plates and the third orthopedic plate that extend away from the third orthopedic plate;
   the method comprising:
      exposing the implanted medical fixation system;
      removing the third orthopedic plate from the first and second orthopedic plates;
      opening a ribcage of the patient;
      performing a thoracic surgical procedure;
      closing the ribcage of the patient by placing a first sternum portion and a second sternum portion in proximity to their presurgical position; and
      fixing the third orthopedic plate to the first and second orthopedic plates.

20. The method of claim 19, wherein removing the third orthopedic plate from the first and second orthopedic plates includes removing the third orthopedic plate by hand.

21. The method of claim 19, wherein removing the third orthopedic plate from the first and second orthopedic plates includes removing the third orthopedic plate using a tool.

22. The method of claim 19, wherein the plurality of bridging plate engagement members and the first and second pluralities of sternal plate engagement members are a metal hook and loop system.

23. The method of claim 19, wherein the plurality of bridging plate engagement members and the first and second pluralities of sternal plate engagement members are a hook and loop system.

* * * * *